US00PP14704P2

(12) United States Plant Patent
Lamb et al.

(10) Patent No.: US PP14,704 P2
(45) Date of Patent: Apr. 20, 2004

(54) SPATHIPHYLLUM PLANT NAMED 'MISS MABEL'

(50) Latin Name: *Spathiphyllum hybrid*
Varietal Denomination: Miss Mabel

(75) Inventors: Ann Elizabeth Lamb, Sebring, FL (US); David R. Lilly, Boynton Beach, FL (US)

(73) Assignee: Twyford International Inc., Santa Paul, CA (US)

( * ) Notice: Subject to any disclaimer, the term of this patent is extended or adjusted under 35 U.S.C. 154(b) by 0 days.

(21) Appl. No.: 10/377,499

(22) Filed: Feb. 28, 2003

(51) Int. Cl.[7] ..... A01H 5/00
(52) U.S. Cl. ..... Plt./364
(58) Field of Search ..... Plt./364

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Spathiphyllum plant named 'Miss Mabel', characterized by its upright, somewhat outwardly spreading and symmetrical plant habit; glossy dark green and rugose leaves with undulate leaf margins; rapid growth rate; freely flowering habit; fragrant white-colored spathes that are positioned just above the foliage on erect peduncles; and good postproduction longevity.

3 Drawing Sheets

Botanical classification/cultivar designation: *Spathiphyllum hybrid* cultivar Miss Mabel.

BACKGROUND OF THE INVENTION

The present Invention relates to a new and distinct cultivar of Spathiphyllum plant, botanically known as *Spathiphyllum hybrid*, and hereinafter referred to by the cultivar name Miss Mabel.

The new cultivar is a product of a planned and controlled breeding program conducted by the Inventors in Apopka, Fla. The objective of the breeding program is to create new Spathiphyllum cultivars with improved plant habit, dark green foliage and rapid growth rate.

The new cultivar originated from a cross-pollination made by the Inventors on Feb. 9, 1998 of the *Spathiphyllum hybrid* cultivar Sparkle, disclosed in U.S. Plant Pat. No. 8,367, as the female or seed parent and the Spathiphyllum hybrid cultivar Sweet Pablo, disclosed in U.S. Plant Pat. No. 10,817, as the male or pollen parent. The cultivar Miss Mabel was discovered and selected by the Inventors as a plant within the progeny of the stated cross-pollination in a controlled environment in Homestead, Fla., on Sep. 23, 1999.

Asexual propagation of the new cultivar by tissue culture since September, 1999, in a laboratory in Sebring, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of 'Miss Mabel'. These characteristics in combination distinguish 'Miss Mabel' as a new and distinct Spathiphyllum cultivar:

1. Upright, somewhat outwardly spreading and symmetrical plant habit.
2. Glossy dark green and rugose leaves with undulate leaf margins.
3. Rapid growth rate.
4. Freely flowering habit.
5. Fragrant white-colored spathes that are positioned just above the foliage on erect peduncles.
6. Good postproduction longevity.

Plants of the new Spathiphyllum differed from plants of the female parent, the cultivar Sparkle, when grown in side-by-side comparisons in Apopka, Fla., in the following characteristics:

1. Plants of the new Spathiphyllum were larger and taller than plants of the cultivar Sparkle.
2. Leaves of plants of the new Spathiphyllum were not as smooth, thick or leathery as leaves of plants of the cultivar Sparkle.
3. Plants of the new Spathiphyllum were more floriferous than plants of the cultivar Sparkle.
4. Spathes of plants of the new Spathiphyllum were larger than spathes of plants of the cultivar Sparkle.
5. Spathes of plants of the new Spathiphyllum were ovate in shape whereas spathes of plants of the cultivar Sparkle were elliptic in shape.

Plants of the new Spathiphyllum differed from plants of the male parent, the cultivar Sweet Pablo, when grown in side-by-side comparisons in Apopka, Fla., in the following characteristics:

1. Plants of the new Spathiphyllum were smaller and shorter than plants of the cultivar Sweet Pablo.
2. Leaves of plants of the new Spathiphyllum were darker green, glossier than leaves of plants of the cultivar Sweet Pablo.
3. Leaves of plants of the new Spathiphyllum were elliptic in shape whereas leaves of plants of the cultivar Sweet Pablo were longer and lanceolate in shape.

4. Spathes of plants of the new Spathiphyllum were ovate in shape whereas spathes of plants of the cultivar Sweet Pablo were lanceolate in shape.

Plants of the new Spathiphyllum can be compared to plants of the Spathiphyllum cultivar Viscount, not patented. In side-by-side comparisons conducted in Apopka, Fla., plants of the new Spathiphyllum differed from plants of the cultivar Viscount in the following characteristics:

1. Plants of the new Spathiphyllum were smaller and shorter than plants of the cultivar Viscount.
2. Leaves of plants of the new Spathiphyllum were smaller, glossier and more rugose than leaves of plants of the cultivar Viscount.
3. Plants of the new Spathiphyllum flowered more readily than plants of the cultivar Viscount.
4. Spathes of plants of the new Spathiphyllum were held just above the foliage whereas spathes of plants of the cultivar Viscount were held well above the foliage.

Plants of the new Spathiphyllum can also be compared to plants of the Spathiphyllum cultivar 6598-1, disclosed in U.S. Plant Patent application filed concurrently. In side-by-side comparisons conducted in Apopka, Fla., plants of the new Spathiphyllum differed from plants of the cultivar 6598-1 in the following characteristics:

1. Plants of the new Spathiphyllum were smaller than plants of the cultivar 6598-1.
2. Leaves of plants of the new Spathiphyllum were smaller, more narrow and glossier than leaves of plants of the cultivar 6598-1.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Spathiphyllum.

The photograph on the first sheet comprises a side perspective view of a typical 10-month old plant of 'Miss Mabel' grown in a 25-cm container.

The photograph on the second sheet comprises a close-up view of a typical inflorescence of 'Miss Mabel'.

The photograph at the top of the third sheet comprises a close-up view of the upper leaf surface of a typical plant of 'Miss Mabel'.

The photograph at the bottom of the third sheet comprises a close-up view of the lower leaf surface of a typical plant of 'Miss Mabel'.

DETAILED BOTANICAL DESCRIPTION

The aforementioned photographs and following observations, measurements and comparisons describe 10-month old plants (from planting rooted tissue-cultured plantlets) grown in Homestead, Fla., in a polypropylene-covered shadehouse and under commercial production conditions in 20-cm containers. During the production of the plants, day temperatures ranged from 70 to 90° F., night temperatures ranged from 65 to 75° F., and light levels were about 1,500 to 2,000 foot-candles.

In the following description, color references are made to The Royal Horticultural Society Colour Chart, 1995 Edition, except where general terms of ordinary dictionary significance are used.

Botanical classification: *Spathiphyllum hybrid* cultivar Miss Mabel.

Parentage:

*Female parent.*—*Spathiphyllum hybrid* cultivar Sparkle, disclosed in U.S. Plant Pat. No. 8,367.

*Male parent.*—*Spathiphyllum hybrid* cultivar Sweet Pablo, disclosed in U.S. Plant Pat. No. 10,817.

Propagation:

*Type.*—By tissue culture.

*Time to initiate roots on a tissue-cultured cutting.*—Summer: About 6 to 8 days at 70 to 90° F. day temperature and 65 to 75° F. night temperature. Winter: About 7 to 10 days at 70 to 90° F. day temperature and 65 to 75° F. night temperature.

*Time to produce a fully-rooted tissue-cultured plantlet.*—Summer: About 70 days at 70 to 90° F. day temperature and 65 to 75° F. night temperature. Winter: About 84 days at 70 to 90° F. day temperature and 65 to 75° F. night temperature.

*Root description.*—Thick, fleshy; lateral branch roots, fine; white in color.

Plant description:

*Plant shape.*—Upright, somewhat outwardly spreading and symmetrical plant habit; intermediate in stature.

*Growth habit.*—Erect when young, becoming somewhat outwardly arching as leaves develop. Freely clumping and full appearance; about nine clumps per plant.

*Plant height.*—About to 55 to 66 cm from soil level to top of leaf plane and about 60 to 70 cm from soil level to spathe apices.

*Plant spread.*—About 80 to 89 cm.

*Growth rate.*—Rapid growth rate; from tissue-cultured plantlets, about ten months are required to produce finished flowering plants in 25-cm containers.

*Foliage description.*—Length: About 28 to 32 cm. Width: About 12.2 to 15.5 cm. Shape: Elliptic. Apex: Acuminate. Base: Cuneate. Margin: Entire; undulate. Aspect: Initially upright, then perpendicular to the petiole; eventually oldest leaves outwardly arching; curved downward towards the apex. Midrib straight or somewhat curved over the length of the leaf. Surface: Rugose; midrib and lateral veins sunken on upper surface and prominent on lower surface. Texture, upper and lower surfaces: Leathery, smooth, glabrous, durable and flexible. Venation pattern: Pinnate. Number of lateral veins per leaf: About 20 pairs. Color: Young and fully expanded leaves, upper surface: 139A; glossy. Young and fully expanded leaves, lower surface: 137B. Midrib, upper surface: 137A to 137B. Midrib, lower surface: 146C. Petiole: Length: About 32 to 36 cm. Diameter, just below the geniculum: About 4 cm. Petiole sheath, length: About 17 to 26 cm; about 5 cm between the top of the petiole sheath and the base of the geniculum. Petiole sheath, diameter: About 1 cm. Petiole sheath, apex: Obtuse to cuneate. Geniculum length: About 5 cm. Geniculum diameter: About 5 mm. Geniculum aspect: Straight to curved. Color: Petiole and sheath: 146B streaked with 137B. Geniculum: 146C tinged with 145A.

Inflorescence description:

*Inflorescence arrangement/quantity.*—Concave spathes with spadices held just above the foliage on erect peduncles. Freely flowering; typically about five open spathes per plant at one time; inflorescences arise from the petiole sheath.

*Time to flower.*—Inflorescences are initiated in the winter and early spring and tend to re-bloom throughout the year in Homestead, Fla.

*Inflorescence longevity.*—Spathes generally maintain white color for about four weeks on the plant. As cut flowers, spathes maintain good substance for about seven days.

*Fragrance.*—Strongly fragrant, sweet, typical of Spathiphyllum; most notable in the morning.

*Inflorescence buds.*—Length: About 14 cm. Diameter: About 1.7 cm. Shape: Spindle-shaped. Color: 155A; midrib, 145B; lateral veins, 155D; towards the apex, 143C.

*Spathe.*—Length: About 14 to 16.5 cm. Width: About 7.5 to 8.7 cm. Depth: About 2 cm. Shape: Ovate to elliptic. Apex: Acuminate; twisted. Base: Cuneate, oblique. Aspect: Concave. Color: Front surface: 155D; midrib, 155D tinged with 191B; apex, 155D tinged with 143C. Back surface: 155D; midrib, 145A; apex, 155D tinged with 143B. Front surface with subsequent development: 144A with 145A; margin, 155D; midrib, 144A; apex, 137C. With development, color becoming entirely darker and more green than, but closest to 144A. Back surface with subsequent development: Darker than, but closest to 144A; margin, 155D; midrib, 137B; apex, 137B.

*Spadix.*—Length: About 9.5 cm. Diameter: About 1.8 cm. Color: 158A gradually becoming closer to 137A with development. Quantity of flowers: About 250 per spadix. Pistillate flowers extend about 3.5 mm beyond the staminate flowers. Pollen: Moderate. Pollen color: 158D darkening to 158A with development. Pistils: Conical; 158A in color.

*Peduncle.*—Length: About 44 to 50 cm. Diameter: About 4 mm. Color: Greener than, but closest to 137C.

*Fruit.*—Type: Berry. Length: About 9 mm. Diameter: About 6 mm. Shape: Ovate. Color: Darker than, but closest to 137A; with subsequent development, tinged with 145C.

*Seed.*—Quantity per fruit: About one to nine. Quantity per inflorescence: About 800 or more. Length: About 3.5 mm. Shape: Reniform. Color: Light brown.

Disease/pest resistance: Plants of the new Spathiphyllum have not been observed to be resistant to pathogens or pests common to Spathiphyllum.

Temperature tolerance: Plants of the new Spathiphyllum have been observed to tolerate temperatures from 45 to 104° F.

It is claimed:

1. A new and distinct cultivar of Spathiphyllum plant named 'Miss Mabel', as illustrated and described.

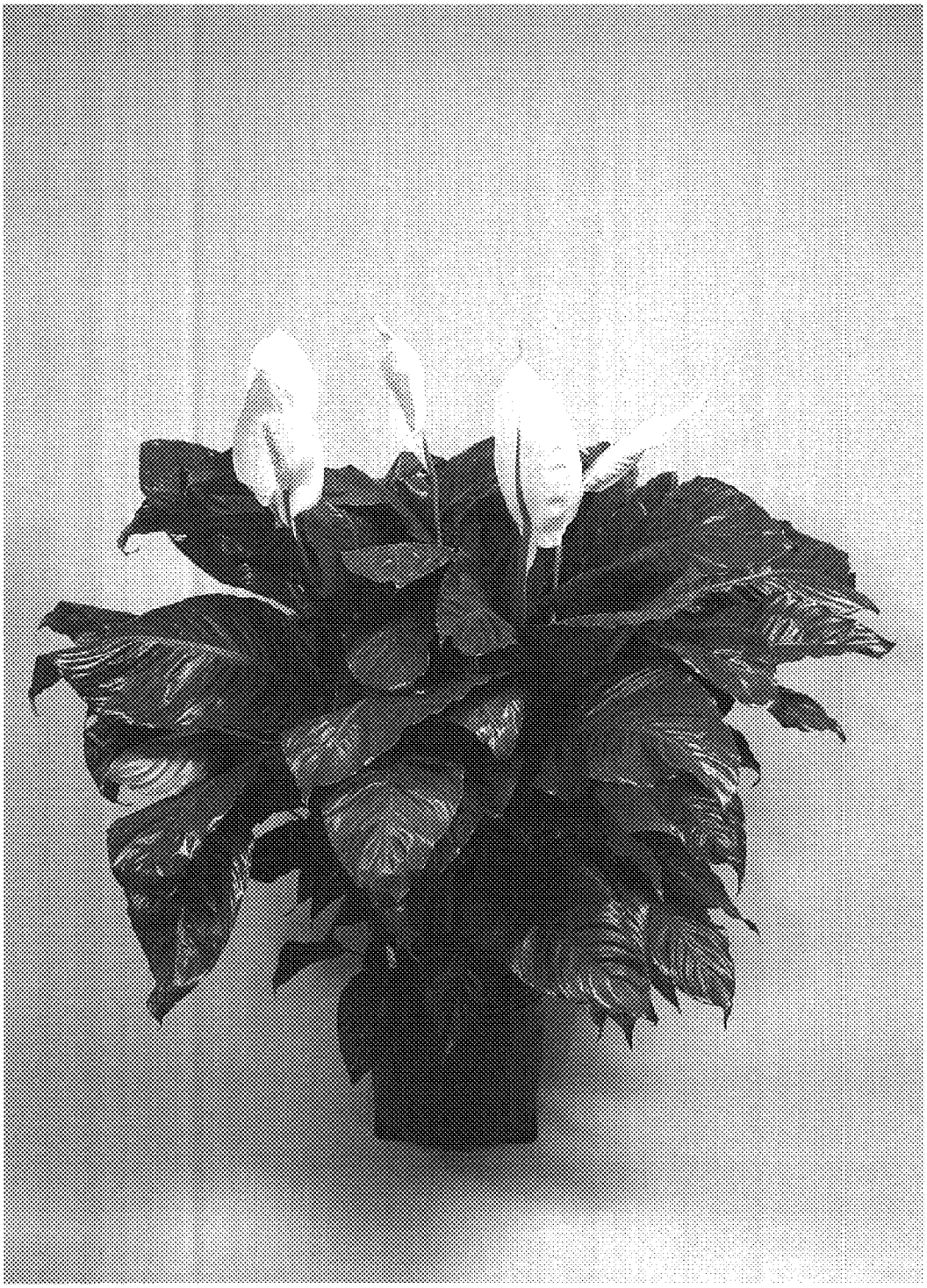

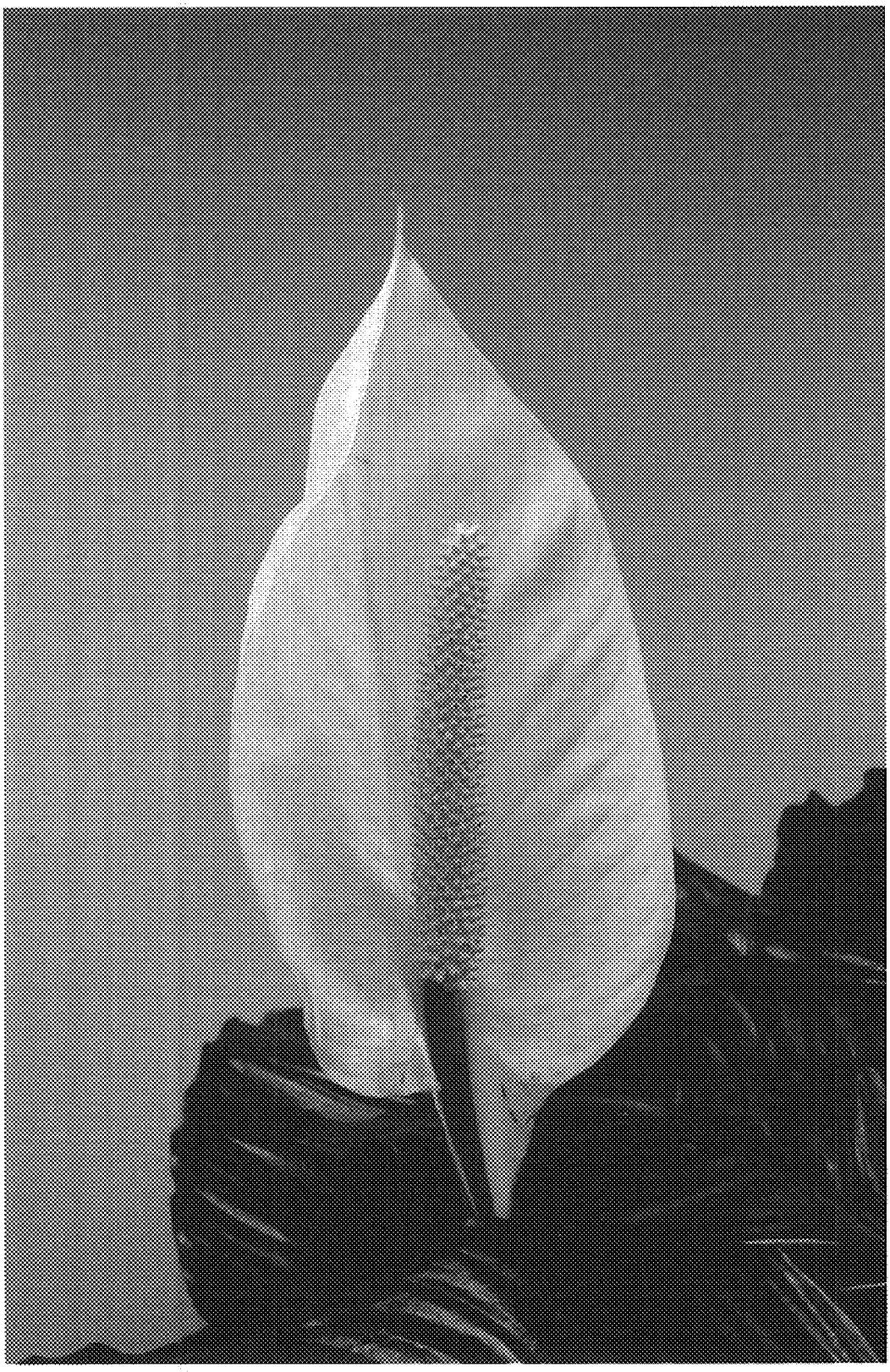

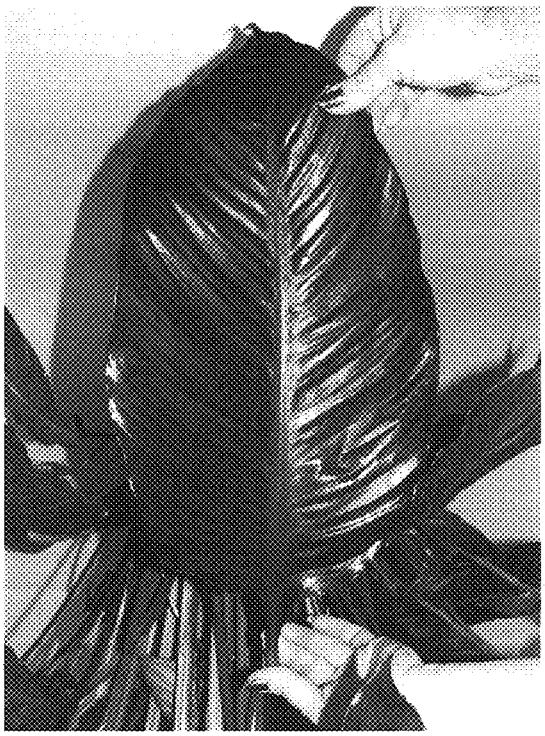
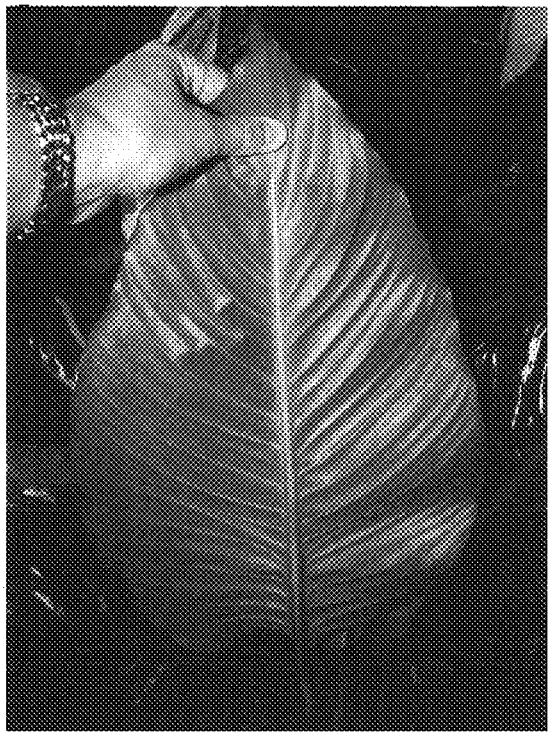

* * * * *